(12) United States Patent
Gozani et al.

(10) Patent No.: US 9,207,195 B2
(45) Date of Patent: *Dec. 8, 2015

(54) HIGH-ENERGY X-RAY-SPECTROSCOPY-BASED INSPECTION SYSTEM AND METHODS TO DETERMINE THE ATOMIC NUMBER OF MATERIALS

(71) Applicant: Rapiscan Systems, Inc., Torrance, CA (US)

(72) Inventors: Tsahi Gozani, Palo Alto, CA (US); Joseph Bendahan, San Jose, CA (US); Craig Matthew Brown, Santa Clara, CA (US); Willem G. J. Langeveld, Menlo Park, CA (US); John David Stevenson, Livermore, CA (US)

(73) Assignee: Rapiscan Systems, Inc., Torrance, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/268,128

(22) Filed: May 2, 2014

(65) Prior Publication Data

US 2014/0341341 A1 Nov. 20, 2014

Related U.S. Application Data

(63) Continuation of application No. 13/033,590, filed on Feb. 23, 2011, now Pat. No. 8,750,454.

(60) Provisional application No. 61/308,152, filed on Feb. 25, 2010.

(51) Int. Cl.
*G01N 23/20* (2006.01)
*G01N 23/087* (2006.01)
*G01N 23/10* (2006.01)
*G01N 23/203* (2006.01)
*G01V 5/00* (2006.01)

(52) U.S. Cl.
CPC .............. *G01N 23/087* (2013.01); *G01N 23/10* (2013.01); *G01N 23/203* (2013.01); *G01N 23/20083* (2013.01); *G01V 5/0016* (2013.01); *G01V 5/0025* (2013.01)

(58) Field of Classification Search
CPC .................. G01N 23/20066; G01N 23/20083; G01V 5/0016; G01V 5/0025; G01V 5/0041
See application file for complete search history.

(56) References Cited

U.S. PATENT DOCUMENTS 4,020,346 A * 4/1977 Dennis ............................. 378/57
4,254,599 A * 3/1981 Maistre ........................ 52/649.1

(Continued)

*Primary Examiner* — Thomas R Artman
(74) *Attorney, Agent, or Firm* — Novel IP

(57) ABSTRACT

The application discloses systems and methods for X-ray scanning for identifying material composition of an object being scanned. The system includes at least one X-ray source for projecting an X-ray beam on the object, where at least a portion of the projected X-ray beam is transmitted through the object, and an array of detectors for measuring energy spectra of the transmitted X-rays. The measured energy spectra are used to determine atomic number of the object for identifying the material composition of the object. The X-ray scanning system may also have an array of collimated high energy backscattered X-ray detectors for measuring the energy spectrum of X-rays scattered by the object at an angle greater than 90 degrees, where the measured energy spectrum is used in conjunction with the transmission energy spectrum to determine atomic numbers of the object for identifying the material composition of the object.

14 Claims, 5 Drawing Sheets

(56) References Cited

U.S. PATENT DOCUMENTS

| | | | |
|---|---|---|---|
| 4,366,382 A * | 12/1982 | Kotowski | 378/57 |
| 4,719,153 A * | 1/1988 | Akasawa et al. | 428/515 |
| 5,046,846 A * | 9/1991 | Ray et al. | 356/326 |
| 5,428,657 A * | 6/1995 | Papanicolopoulos et al. | 378/86 |
| 5,600,700 A * | 2/1997 | Krug et al. | 378/57 |
| 5,638,420 A * | 6/1997 | Armistead | 378/57 |
| 5,838,758 A * | 11/1998 | Krug et al. | 378/53 |
| 6,069,936 A * | 5/2000 | Bjorkholm | 378/98.9 |
| 6,118,850 A * | 9/2000 | Mayo et al. | 378/83 |
| 6,347,132 B1 * | 2/2002 | Annis | 378/57 |
| 6,442,233 B1 * | 8/2002 | Grodzins et al. | 378/57 |
| 6,556,653 B2 * | 4/2003 | Hussein | 378/90 |
| 6,567,496 B1 * | 5/2003 | Sychev | 378/57 |
| 6,785,357 B2 * | 8/2004 | Bernardi et al. | 378/57 |
| 6,973,158 B2 * | 12/2005 | Besson | 378/16 |
| 6,987,833 B2 * | 1/2006 | Du et al. | 378/98.9 |
| 7,103,137 B2 * | 9/2006 | Seppi et al. | 378/9 |
| 7,130,484 B2 * | 10/2006 | August | 382/266 |
| 7,286,638 B2 * | 10/2007 | Ledoux et al. | 378/88 |
| 7,322,745 B2 * | 1/2008 | Agrawal et al. | 378/198 |
| 7,366,282 B2 * | 4/2008 | Peschmann | 378/57 |
| 7,368,717 B2 * | 5/2008 | Verbinski et al. | 250/358.1 |
| 7,369,642 B2 * | 5/2008 | Eilbert et al. | 378/57 |
| 7,381,962 B2 * | 6/2008 | Goldberg | 250/370.09 |
| 7,406,192 B2 * | 7/2008 | Schmiegel et al. | 382/152 |
| 7,440,544 B2 * | 10/2008 | Scheinman et al. | 378/57 |
| 7,453,987 B1 * | 11/2008 | Richardson | 378/98.9 |
| 7,483,511 B2 * | 1/2009 | Bendahan et al. | 378/57 |
| 7,492,682 B2 * | 2/2009 | Osakabe | 369/47.53 |
| 7,492,862 B2 * | 2/2009 | Bendahan | 378/57 |
| 7,492,934 B2 * | 2/2009 | Mundy et al. | 382/128 |
| 7,522,696 B2 * | 4/2009 | Imai | 378/8 |
| 7,526,064 B2 * | 4/2009 | Akery | 378/57 |
| 7,555,099 B2 * | 6/2009 | Rothschild et al. | 378/90 |
| 7,653,545 B1 * | 1/2010 | Starkie | 704/275 |
| 7,693,261 B2 * | 4/2010 | Robinson et al. | 378/88 |
| 7,750,294 B2 * | 7/2010 | Bright et al. | 250/308 |
| 7,809,103 B2 * | 10/2010 | Du et al. | 378/53 |
| 7,844,027 B2 * | 11/2010 | Harding et al. | 378/9 |
| 7,965,816 B2 * | 6/2011 | Kravis et al. | 378/87 |
| 8,116,428 B2 * | 2/2012 | Gudmundson et al. | 378/53 |
| 8,179,597 B2 * | 5/2012 | Namba et al. | 359/383 |
| 8,233,586 B1 * | 7/2012 | Boas | 378/4 |
| 2008/0298546 A1 * | 12/2008 | Bueno et al. | 378/57 |
| 2010/0034353 A1 * | 2/2010 | Kravis et al. | 378/87 |
| 2010/0295689 A1 * | 11/2010 | Armistead et al. | 340/600 |
| 2011/0096906 A1 * | 4/2011 | Langeveld | 378/82 |
| 2011/0235777 A1 * | 9/2011 | Gozani et al. | 378/53 |
| 2011/0305318 A1 * | 12/2011 | Robinson | 378/88 |

\* cited by examiner

HIGH-ENERGY X-RAY-SPECTROSCOPY-BASED INSPECTION SYSTEM AND METHODS TO DETERMINE THE ATOMIC NUMBER OF MATERIALS

CROSS-REFERENCE

The present application is a continuation of U.S. patent application Ser. No. 13/033,590, filed on Feb. 23, 2011, now U.S. Pat. No. 8,750,454, issued on Jun. 10, 2014, which, in turn, relies on U.S. Patent Provisional Application No. 61/308,152, filed on Feb. 25, 2010, for priority. All priority applications are hereby incorporated by reference in their entirety.

FIELD OF THE INVENTION

The present specification generally relates to the field of radiant energy imaging systems, and more specifically to a system that makes use of the full spectrum of X-ray energies transmitted or transmitted and scattered for improved determination of the atomic number of materials, such as objects in cargo containers.

BACKGROUND OF THE INVENTION

X-ray inspection systems are presently limited in their ability to detect and distinguish contraband, drugs, weapons, explosives, and other items of interest concealed in cargo from benign materials. There is further an interest in inspecting cargo for manifest verification purposes to ensure appropriate customs duty is paid.

The intensity of the transmitted X-rays is related to the areal density (i.e. density×thickness) and the atomic number (Z) of the materials they traverse. Radiographs produced by conventional X-ray systems are often difficult to interpret, because objects are superimposed and no Z information is provided. Therefore, a trained operator must study and interpret each image to render an opinion on whether or not a target of interest, or a threat, is present. When a large number of such radiographs are to be interpreted, such as at high-traffic transit points and ports, these inherent difficulties, combined with operator/screener fatigue and distraction, can compromise detection performance. There is a need for automatic detection and/or screener-assist tools for detection of threats and other targets, in order to improve the efficiency and accuracy of operators, and to reduce the number of operators needed for the detection.

Methods known to those skilled in the art for obtaining useful Z-information include the use of dual-energy X-ray sources, and dual-species technologies (X-ray inspection combined with neutron inspection). However, these methods do not readily allow accurate determination of the actual Z of the cargo contents, but rather yields an average Z that represents a mix of the various materials in the X-ray beam path. Thus, these methods are not efficient.

Therefore, X-ray inspection systems currently available in the art provide limited accuracy for detection of items of interest. Further, these systems do not effectively detect high atomic-number ("high-Z") materials. Detecting such materials, particularly smuggled special nuclear materials (SNM) that could potentially be used to make a weapon, or materials used to shield their radioactive emissions, is a very complex task. One of the materials of greatest concern, highly enriched uranium (HEU), has a relatively low level of radioactivity. Plutonium, another nuclear weapons grade material, has a higher specific activity and higher-energy emissions. However, it can be shielded by employing a combination of high-Z materials for shielding gamma rays and low-atomic number ("low-Z") neutron absorbers for shielding neutrons produced by spontaneous fission. Thus, it is very difficult to detect shielded or concealed materials.

It is therefore desirable to have improved methods and systems for effectively detecting high-Z materials, particularly accounting for the possibility that such materials may be shielded by a combination of high-Z materials for shielding gamma rays and low-Z neutron absorbers for shielding neutrons.

SUMMARY OF THE INVENTION

In one embodiment, the application discloses an X-ray scanning system for identifying material composition of an object being scanned.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings.

DESCRIPTION OF THE INVENTION

The present specification is an improved method of screening cargo that uses spectroscopic information from only the transmitted, or from both the transmitted and scattered, high-energy X-ray beam to provide enhanced detection capabilities of contraband, threats and other targets of interest, which are difficult to detect with current X-ray methods and/or through passive radiation detection techniques known in the art. The system of the present invention delivers improved detection performance for objects of interest either automatically or as a tool to assist an operator, while at the same time reducing false-alarm rate.

In general, for a given thickness of an absorber, the higher the atomic number, the higher the attenuation of the high end of the X-ray spectrum. Therefore, the transmitted X-ray spectrum is affected by variations in the atomic number of items of various materials inside the cargo.

The present specification detects and measures the entire energy spectrum of the transmitted or transmitted and scattered X rays, and identifies materials that are in the beam path and their probable atomic number and areal density. The energy spectrum of the X-rays transmitted through and scattered by a cargo contains a wealth of information on the material properties of the cargo they traverse. Theoretical analysis and actual measurements demonstrate that the X-ray spectrum of the transmitted X-rays is very sensitive to the Z of the cargo materials.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
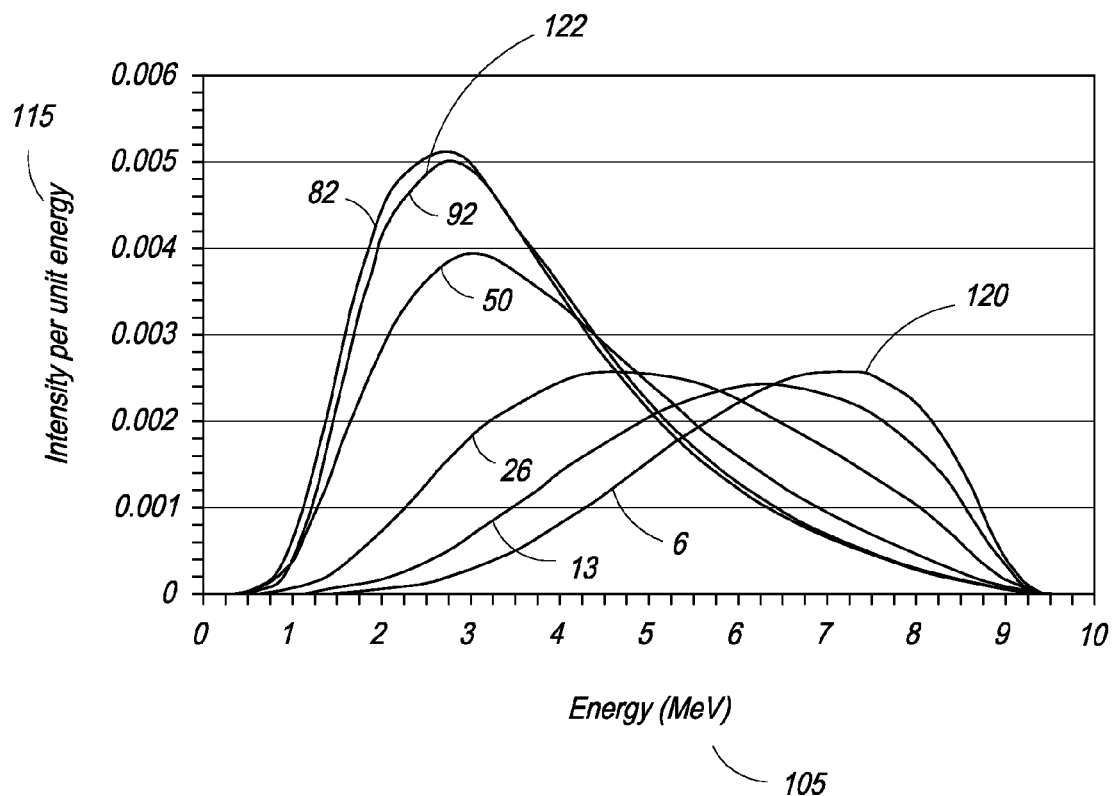
FIG. 1 illustrates normalized intensity of a transmitted X-ray beam per unit energy in relation to energy, in MeV, for different absorbers.
Figure 2:
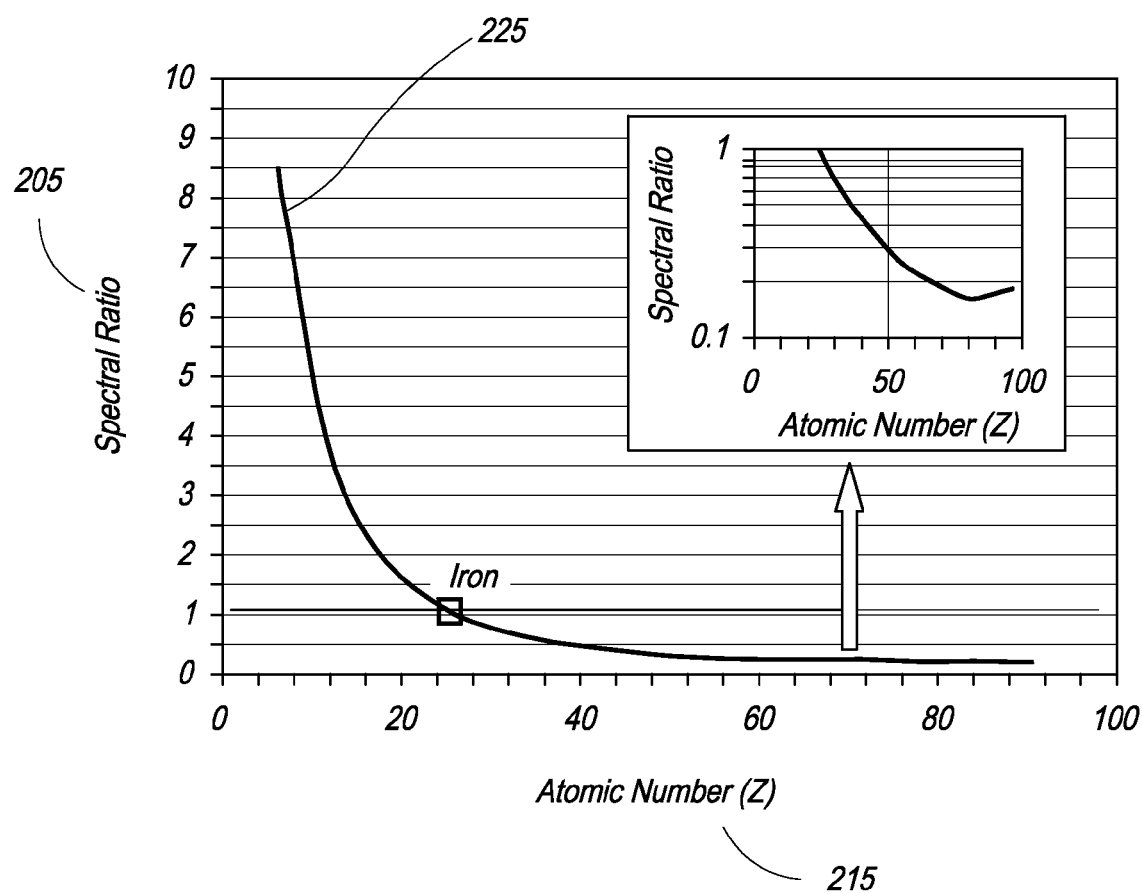
FIG. 2 illustrates a spectral ratio of the amplitudes of the low and high energy regions in the transmission spectrum shown in FIG. 1, plotted against atomic number.

Referring to FIG. 1, the normalized intensity of the transmitted X-ray beam per unit energy 115 is shown in relation to the energy, in MeV, 105 for different absorbers. As shown, for 9 MV X-ray transmission spectra, carbon (Z=6) has a very different spectrum from that of uranium (Z=92). Referring to FIG. 2, a spectral ratio 205 of the amplitudes of the low and high energy regions in the transmission spectrum (shown in FIG. 1), plotted against atomic number 215, is shown, demonstrating a very high sensitivity 225.

Figure 3:
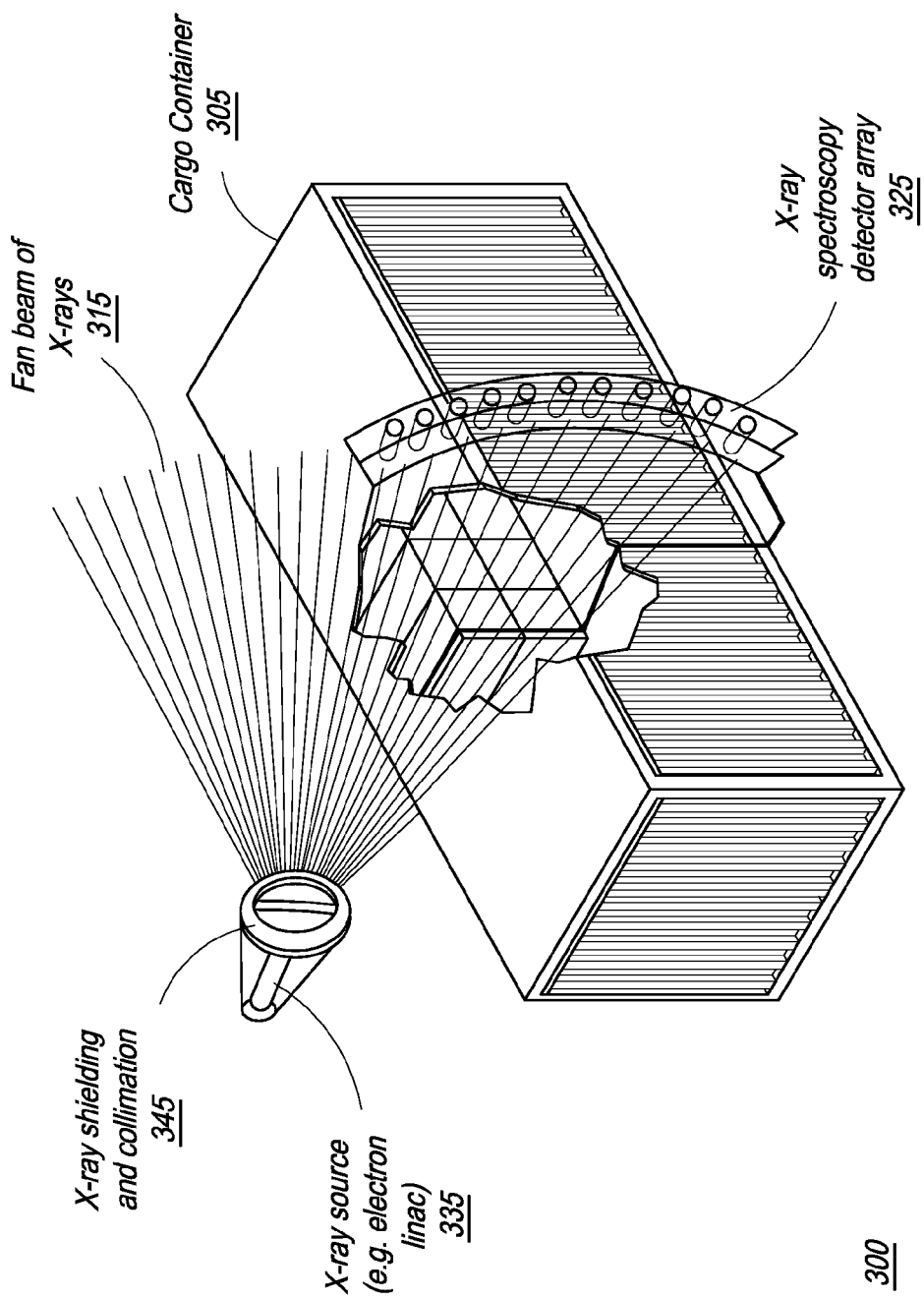
FIG. 3 illustrates the X-ray transmission spectroscopy system scanning a cargo container, in accordance with an embodiment of the present invention.

Referring to FIG. 3, the X-ray transmission spectroscopy system 300 of the present invention is shown scanning a cargo container 305. The system 300 employs a collimated X-ray source 335 and measures the energy spectra of the transmitted X-rays 315 using fast spectroscopic detectors 325 with predetermined energy resolution. The higher the X-ray source energy 335, the stronger the effect. In another embodiment, the system 300 measures the energy spectrum of X-rays 315 scattered at a small angle with respect to the original X-ray direction. It should be appreciated that the X-ray source can be of any energy level, but is preferably an energy level of 1 MeV or higher. Further, the X-ray source can be a pulsed source like an electron linac, a continuous X-ray emission source, an intensity-modulated X-Ray source, such as the one disclosed in U.S. patent application Ser. No. 12/484,172 which is incorporated herein by reference, or any other type of X-ray source, and can use any beam geometry, including pencil, fan, conical, or other geometries.

Figure 4:
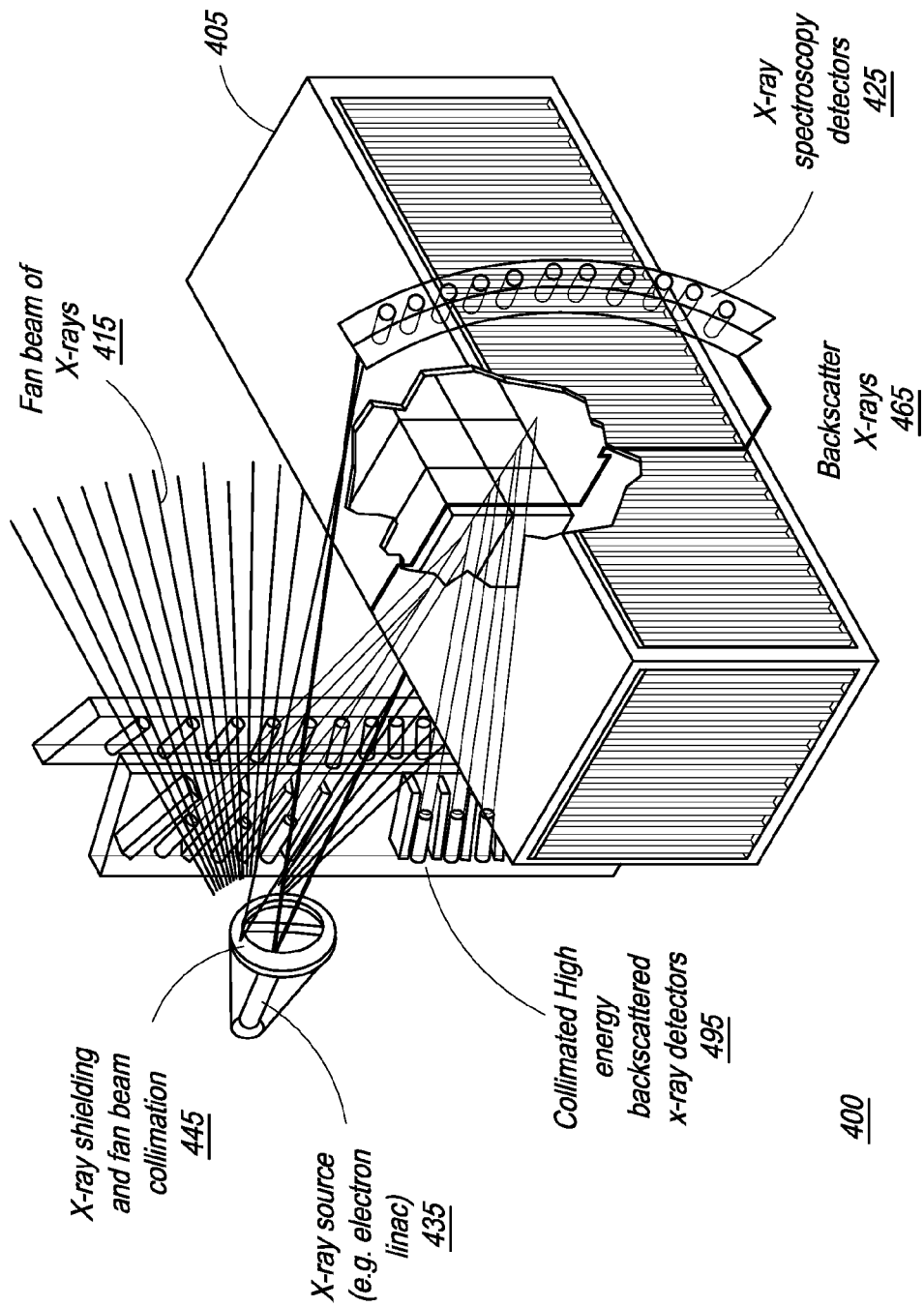
FIG. 4 illustrates the X-ray transmission spectroscopy system scanning a cargo container, in accordance with another embodiment of the present invention.
Figure 5:
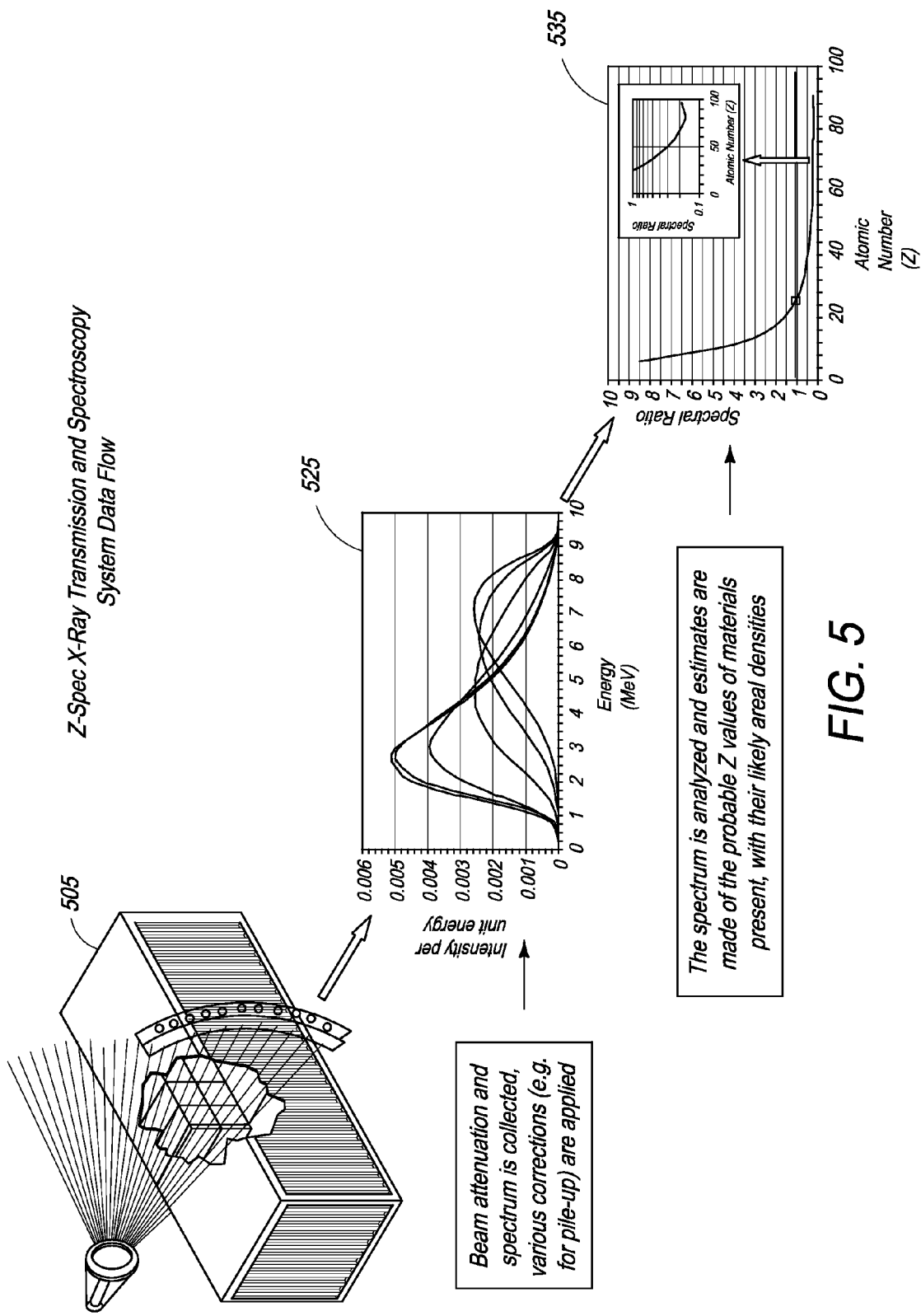
FIG. 5 illustrates an exemplary data flow for said X-ray transmission spectroscopy system.

Referring to FIG. 4, in another embodiment of the present invention, a system 400 measures both the transmitted X-ray energy spectrum and the large-angle (>90°) scattered energy spectrum. Measuring both sets of the spectra simultaneously further enhances the Z sensitivity of system 400. In FIG. 4, the X-ray transmission spectroscopy system 400 is shown scanning a cargo container 405. The system 400 employs X-ray sources 435 and measures the energy spectra of the transmitted X-rays 415 using fast spectroscopic detectors 425 with predetermined energy resolution. The system 400 also measures the energy spectra of backscattered X-rays 465 with respect to the original X-ray direction, as determined using X-ray shielding and collimation 445, using collimated high energy backscattered X-ray detectors 495. The energy spectra of some of the X-rays scattered at an angle greater than 90 degrees are measured in addition to the transmitted energy spectra. Information from the two sets of spectra derived from X-rays 415, 465 can be combined to greatly increase the Z sensitivity. In this embodiment, collimated detectors 495 are used which measure the energy spectra of the high-energy back-scattered X-ray radiation 465. By way of example, it may be necessary to move the cone of view up or down in order to scan an entire slice of the cargo illuminated by the X-ray fan beam. Other scanning approaches are possible.

The proposed method can be used with pulsed X-ray sources, using, e.g., electron linear accelerators (linacs), as well as CW (continuous wave) X-ray sources. Conventional linacs produce X-rays in short bursts of radiation (usually less than 5 μs). In this case, the instantaneous rate of X-rays arriving at the detector during the pulse can be very high. This rate is especially high when no cargo is present ("in air") and for lightly loaded containers where the X-ray transmission is high. If the count rate is high enough, it is possible that the signals in the X-ray detector due to two or more X-rays overlap in time, in such a way that the energy of the individual X-rays cannot be reliably measured. This effect is exacerbated if the X-ray detectors and their read-out systems are not sufficiently fast. Even in this case, however, material discrimination is still possible within the range of X-ray attenuations by the cargo where the count rate does not exceed this threshold. Alternatively, a shield can be put in front of the detectors in order to reduce the count rate, but this may be done at the expense of being able to perform spectroscopy at high attenuation.

CW sources produce X-rays continuously in time. For such sources, the instantaneous count rate is lower than for pulsed sources with the same (integrated) output. This allows extending the applicability of the present method to a wider range of cargo attenuations.

In one embodiment of the present invention, a secondary array of very fast detectors is used to obtain the spectral information, in addition to the primary detector array used for radiography. The first array of detectors, which generate a high-resolution radiographic image, may be less fast relative to the second array of detectors and need not measure spectra. In this manner, very fast detectors can be used for transmission spectroscopy, e.g. plastic scintillators with photo-multiplier tubes. In such a system, the spatial resolution of the spectroscopic system may not match that of the radiography system, for example, because, if photomultiplier tubes are used, they tend to be relatively large compared to the photo-diodes typically used for radiography. The spectroscopic array could be placed beside the radiographic array, or behind it. In this embodiment, the traditional high-resolution radiographic image is maintained with a lower-resolution spectroscopic image. This may provide a good trade-off between capability and cost.

In another embodiment of the system, for example in a mobile systems with a much lower penetration requirement, one can use slower, but denser, scintillator materials, such as $LaBr_3$ (Lanthanum Bromide) or LYSO (Lutetium Yttrium Ortho-Silicate). This allows one to make compact transmission spectroscopy detectors with better spatial resolution. In this embodiment, the imaging and transmission spectroscopy arrays can be combined into a single array, since these scintillator materials are also suitable for use in the primary imaging system.

Detector arrays that are only used for imaging usually employ slow scintillators, such as CsI (Cesium Iodide) or $CdWO_4$ (Cadmium Tungstate), with unbiased PIN photo-diodes which are used in "integration" mode, i.e. they measure the total amount of energy deposited in them during an accelerator pulse when a pulsed source is used, or during a fixed time period when a CW source is used. Imaging detector arrays that are also used for transmission spectroscopy must use dense but faster scintillators, such as the already mentioned LaBr3 or LYSO, and a faster light detector, such as a biased PIN diode. Alternate embodiments include utilization of avalanche photodiodes and/or silicon drift detectors. It should be appreciated, however, that any detector material and read-out method can be used that is fast enough for the intended purposes as described herein. This includes any scintillator/photo-detector combination, as well as any semiconductor device suitable for detecting X-rays and measuring their energy, which are fast enough for the intended purposes as described herein.

Combining the detector arrays accomplishes high-resolution radiography and transmission spectroscopy with a single detector array. A disadvantage is the possibly high cost of a large number of spectroscopic channels. If high-resolution radiographic images are not required, large detectors can be used.

Regardless of the detectors used, the spectroscopic information is analyzed using one of at least two analysis methods. In the first case, material separation is achieved employing various spectral features. The X-ray transmission spectra are normalized by dividing each spectrum by the measured total transmitted X-ray or energy flux. Using such a normalization method, the spectral shapes are unique for each material Z. This approach provides a good separation of high-Z materials from lower-Z materials, since the spectra have distinctively different peak locations, intensities, widths, statistical skewness and other features. For example, the mean energies of spectra of high-Z materials are lower, and the peaks are narrower and have higher amplitudes. There is very good separation between medium-Z (e.g. iron) and high-Z materials, and between medium-Z and hydrogenous materials. An example of the Z dependence of a spectral feature (in this case the ratio of the amplitudes of the lower and higher energy regions of the spectrum) is shown in the FIG. 2. There is a very strong correlation between the feature selected here and the atomic number.

In an alternate analysis method, the spectrum for at least one detector is fitted to an expected spectrum. The expected spectrum is computed from the incident spectrum of X-rays produced by the source by calculating the attenuated X-ray spectrum through specific materials and correcting for the detector response. The areal densities of the candidate materials are parameters of the fit. In this approach, an initial material-composition estimate is computed based on the observed transmission. With a list of constraints, including non-negative thickness, a least-squares (or other) statistical minimization is performed until the difference between the computed and observed spectra is minimized. In some embodiments, the minimization is performed in two or more steps. In the first step, a small number of material parameters are used to serve as an estimate, and in subsequent iterations an increasing number of material parameters are used. In the final iteration, all the materials in the considered set are used.

In both analysis methods, the results are given as combinations of areal densities of materials that are likely to be present in the cargo, for example, and not limited to such values or materials, 100 grams/cm$^2$ of wood and 50 grams/cm$^2$ of steel.

In principle, employing detectors with sufficient energy resolution and with high counting statistics, it is possible to determine the complete elemental composition of cargo along the beam path. In practice (with current technology), materials with similar atomic numbers cannot easily be distinguished. Typical detection groups include organic materials, or Low Z: ($Z \leq 10$), Medium-low Z: $11 \leq Z \leq 19$, Medium Z: $20 \leq Z \leq 39$, Medium-high Z: $40 \leq Z \leq 72$, and High-Z: ($Z \geq 73$).

The number of Z-groups and their bounds may be chosen in different ways, based on the energy of the X-ray generating source, whether it is pulsed or continuous, its intensity, the type and size of the spectroscopic detectors, inspection time, etc.

The technology described above provides a system and methods to obtain enhanced material discrimination employing X-rays. The system and methods of this invention improve the detection of contraband, threats and other targets, allow easier cargo-manifest verification, and facilitate automatic detection. These technical advantages translate to increased operator accuracy and efficiency, leading to a reduction of man power, increased contraband interdiction and increased customs-duty revenues.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An X-ray scanning system for identifying material composition of an object being scanned comprising:
    at least one X-ray source for projecting an X-ray beam on the object, at least a portion of the projected X-ray beam being transmitted through the object;
    at least two arrays of detectors, wherein one of said at least two arrays of detectors comprises scintillator material having at least one of Lanthanum Bromide or Lutetium Yttrium Ortho-Silicate, measures an energy spectra of the transmitted X-rays, and generates an image having a first resolution, and wherein a second of said at least two arrays of detectors comprises scintillator material having at least one of Cesium Iodide or Cadmium Tungstate and generates an image having a second resolution, said second resolution being greater than the first resolution; and
    a processor for identifying the material composition of said object wherein said processor determines the material composition using said spectra.

2. The X-ray scanning system of claim 1 wherein the second one of said at least two arrays of detectors detects said transmitted X-rays and generates a transmission image.

3. The X-ray scanning system of claim 2 wherein the processor determines the material composition using said spectra and said transmission image.

4. The X-ray scanning system of claim 2 further comprising an array of collimated backscatter X-ray detectors for measuring energy spectra of X-rays scattered by the object at an angle greater than 90 degrees and generating backscatter data therefrom.

5. The X-ray scanning system of claim 4 wherein the processor determines the material composition using said spectra, said backscatter data, and said transmission image.

6. The X-ray scanning system of claim 1 wherein said identification of the material composition comprises at least one of determining an atomic number of at least some material in said object, determining an atomic number range of at least some material in said object, or determining an areal density of at least some material in said object.

7. The X-ray scanning system of claim 1 wherein said processor determines the material composition using said spectra by:
    receiving said energy spectra;

normalizing said energy spectra using a value; and determining the material composition of the object based upon said normalized energy spectra and a plurality of known spectra.

8. The X-ray scanning system of claim 7 wherein said normalized energy spectra is compared to the plurality of known spectra and wherein the material composition is identified based upon said comparison.

9. The X-ray scanning system as claimed in claim 1, wherein the X-ray beam has a pencil shape, fan shape, or conical shape.

10. The X-ray scanning system as claimed in claim 1, wherein the X-ray source comprises at least one of a continuous X-ray source, pulsed X-ray source, intensity-modulated X-ray source, electron linear accelerator, or X-ray source having an energy level of 1 MeV or greater.

11. The X-ray scanning system of claim 1 wherein said processor determines the material composition using said spectra by:

receiving said energy spectra;

fitting at least one of said energy spectra to an expected energy spectrum, wherein said expected energy spectrum is at least one of a plurality of previously measured X-ray spectra generated by transmitting and detecting X-rays through known materials and correcting said detected X-rays to account for variations in detectors; and identifying the material composition of the object based upon said fitting.

12. The X-ray scanning system of claim 11 wherein said processor generates a first estimate of said material composition based on at least one of said spectra of the transmitted X-rays and not based on said fitting.

13. The X-ray scanning system of claim 11 wherein said processor identifies the material composition of the object by minimizing differences between at least one of said spectra of the transmitted X-rays and said expected energy spectrum.

14. The X-ray scanning system of claim 11 wherein each of said expected energy spectrum is specific to a particular material.

\* \* \* \* \*